(12) United States Patent
Sugano et al.

(10) Patent No.: US 6,451,336 B2
(45) Date of Patent: *Sep. 17, 2002

(54) METHOD FOR INCREASING BROWN FAT, COMPRISING ADMINISTERING CONJUGATED LINOLEIC ACID AS ACTIVE INGREDIENT

(75) Inventors: Michihiro Sugano, Kumamoto; Masanobu Sakono, Miyazaki; Kazunori Koba, Nagasaki; Hitoshi Okuyama, Tokyo-To; Masaaki Kasai, Nagoya; Toshio Iwata, Tokyo-To, all of (JP)

(73) Assignee: Rinoru Oil Mills Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/560,902

(22) Filed: Apr. 28, 2000

(30) Foreign Application Priority Data

Apr. 28, 1999 (JP) .......................................... 11-122794

(51) Int. Cl.$^7$ .......................... A61K 31/00; A61K 9/48; A61K 9/20; A61K 9/14; A23K 1/00
(52) U.S. Cl. ...................... 424/439; 424/442; 424/451; 424/464; 424/489
(58) Field of Search ................................. 424/439, 442, 424/451, 464, 489

(56) References Cited

U.S. PATENT DOCUMENTS

| | | | | | |
|---|---|---|---|---|---|
| 5,626,849 | A | * | 5/1997 | Hastings et al. | 424/195.1 |
| 5,760,082 | A | * | 6/1998 | Cook et al. | 514/560 |
| 5,814,663 | A | * | 9/1998 | Cook et al. | 514/560 |

* cited by examiner

*Primary Examiner*—Thurman K. Page
*Assistant Examiner*—Rachel M. Bennett
(74) *Attorney, Agent, or Firm*—Foley & Lardner

(57) ABSTRACT

There is provided an agent for increasing brown fat, comprising a conjugated linoleic acid as an active ingredient.

8 Claims, No Drawings

METHOD FOR INCREASING BROWN FAT, COMPRISING ADMINISTERING CONJUGATED LINOLEIC ACID AS ACTIVE INGREDIENT

BACKGROUND OF THE INVENTION

1. Field of the Invention

The present invention relates to an agent for increasing brown fat, comprising a conjugated linoleic acid as an active ingredient. More particularly, the present invention relates to an agent for increasing brown fat, comprising a conjugated linoleic acid as an active ingredient, which agent can increase brown fat cells capable of consuming extra energy and producing heat to prevent obesity, and use of the agent in the field of foods.

2. Background Art

In recent years, patients suffering from obesity have been increased also in Japan, and this is becoming a serious social problem. Obesity derived from such factors as increased ingestion (hyperphagia), reduced excercise (lack of excercise), and a fluctuation in generation of body heat causes accumulation of a large amount of body fat. This is causative of arteriosclerosis, hypertension, diabetes, and cardiac diseases, and, in some cases, leads to complications, such as angiopathy, neuropathy, and aphylaxis.

Fat is stored in adipose tissues. Adipose tissues are classified into two types which are utterly different from each other in function. One of the adipose tissues is a white adipose tissue which occupies the major part of the adipose tissues and functions to accumulate extra energy, and the other adipose tissue is a brown adipose tissue which has a function opposite to that of the white adipose tissue, that is, functions to consume extra energy. The brown adipose tissue is significantly found in infancy, and the level thereof decreases with aging. The brown adipose tissue is present in the back of the neck, a portion around shoulder blade in the back, axilla, periphery of the heart, and periphery of the kidney, and the total weight thereof is as small as about 40 g. This brown adipose tissue is governed by a sympathetic nervous system, and functions to generate heat for body temperature retention purposes and, in addition, to burn extra energy, thereby preventing obesity. Increasing and developing this brown adipose tissue are a great aid in eliminating obesity and are expected to prevent or reduce obesity.

On the other hand, conjugated linoleic acids are isolated from fried meats (Y. L. Ha et al., Carcinogenesis, 8, 1881-1887, 1987), and, up to now, the following reports have been made on various activities of the conjugated linoleic acids: ① anti-carcinogens (Cancer Research, 51, 6118-6124, 1991); ② method for enhancing animal feed efficiency (Japanese Patent No. 2745245); ③ method for storing foods and a preservative for use therein (Japanese Patent No. 1935402); ④ methods for preventing weight loss, reduction in weight gain, and anorexia due to immune stimulation (U.S. Pat. No. 5,430,066); ⑤ method for reducing body fat (U.S. Pat. No. 5,554,646); ⑥ methods for maintaining and enhancing bone mineral content (U.S. Pat. No. 5,804,210); and ⑦ method for reducing secretion of apolipoprotein B (U.S. Pat. No. 5,837,733). So far as the present inventors know, however, there is no report such that the conjugated linoleic acids act to increase brown fat.

Accordingly, it is an object of the present invention to provide pharmaceutical preparations, foods, and feed which can increase and develop brown adipose tissues to prevent and remedy obesity.

SUMMARY OF THE INVENTION

The present inventors have repeated extensive and intensive studies using brown adipose tissues as an index of the usefulness in prophylaxis and therapy of obesity and, as a result, have found that conjugated linoleic acids have high activity to increase brown fat and thus are useful for the prophylaxis of obesity. This has led to the completion of the present invention.

Thus, according to the present invention, there is provided an agent for increasing brown fat, comprising a conjugated linoleic acid as an active ingredient.

DETAILED DESCRIPTION OF THE INVENTIOIN

Conjugated linoleic acids (CLA) usable in the present invention include 9,11-octadecadienoic acid, 10,12-octadecadienoic acid, and mixtures of said compounds. Among others, 9c,11t/9t, 11c-octadecadienoic acid is preferred.

Forms of the conjugated linoleic acid usable herein include fatty acids, mono-, di-, or triglycerides, sodium salts, potassium salts, calcium salts, phospholipids, and lysophospholipids, and a mixture of two or more of them. Among them, fatty acids, triglycerides, phospholipids, and calcium salts are preferred. Further, derivatives of conjugated linoleic acids, for example, ascorbic acid derivatives and mitomycin C derivatives, may also be used.

The "agent for increasing brown fat, comprising a conjugated linoleic acid as an active ingredient" according to the present invention may be used as pharmaceutical preparations and, in addition, as antiobesitic foods.

One of embodiments of the antiobesitic food is a conjugated linoleic acid-containing fat-and-oil product obtained by subjecting a linoleic acid-containing fat and oil (for example, a safflower oil) to an alkali conjugation reaction to convert linoleic acid in the fat and oil to conjugated linoleic acid. The "alkali conjugation reaction" is a reaction such that a fatty acid is converted to a conjugated fatty acid by isomerization of the fatty acid in an alkali-organic solvent solution. In a conventional representative method used to this end, potassium hydroxide is used as the alkali, and ethylene glycol is used as the organic solvent (J. Am. Oil Chem. Soc., 36, 631, (1959) and Standard Methods for the Analysis of Oils, Fats and Derivatives 2.4.16-17, Abstract of the 34th Annual Meeting of Japan Oil Chemists' Society, p. 171 (1995)). Further, the present inventors have previously proposed a process for producing conjugated linoleic acid with improved conversion wherein propylene glycol is used as an organic solvent (Japanese Patent Application No. 288094/1996). When the starting fat and oil is a safflower oil, the content of CLA in a conjugated linoleic acid-containing fat and oil obtained by the above alkali conjugation method is generally 10 to 95%, preferably 50 to 80%, with the balance comprising palmitic acid, stearic acid, oleic acid, unconjugated linoleic acids, etc.

When the "agent for increasing brown fat, comprising a conjugated linoleic acid as an active ingredient" according to the present invention is used as pharmaceutical preparations, the conjugated linoleic acid may be used in combination with other ingredients, for example, medicinal diluents (lactose, starch, dextrin, gum arabic or the like). The agent for increasing brown fat may be used in the form of tablets, capsules, or liquids.

When the agent for increasing brown fat according to the present invention is used as foods or feeds, the content of the conjugated linoleic acid in the food or feed is generally 0.001 to 100% by weight, preferably 0.01 to 80% by weight.

In any of the use of the agent for increasing brown fat according to the present invention in foods, pharmaceutical preparations, feeds, and pet foods, the intake of the conjugated linoleic acid is generally 0.01 to 3% by weight, preferably 0.05 to 1% by weight, based on the weight of diet.

The following experimental example demonstrates that conjugated linoleic acid can increase the weight of brown adipose tissues.

EXAMPLE 1

Sprague-Dawley male rats of four weeks of age were pre-bred, and then divided into two groups (each group consisting of 8 rats), a 1.0% linoleic acid group (a control group) and a 1.0% CLA group. The experimental diet shown in Table 1 and water were then freely fed to these two groups of rats. As shown in Table 2, the CLA used was composed mainly of two types, 9c,11t/9t,11c-18:2 and 10t,12c-18:2. Four weeks after the initiation of feeding, the 8 rats constituting each group were sacrificed, and the organs were taken out.

As a result, there was no significant difference in intake and weight gain between the two groups.

Further, as shown in Table 3, there was no difference in the weight of tissues of liver, kidney, heart, lungs, spleen, and brain between the two groups. On the other hand, for the CLA-supplemented group, as compared with the control group, the weight of adipose tissues around the kidney, which are white adipose tissues, was significantly decreased, and the weight of brown adipose tissues in the back was significantly increased.

Further, the activity of carnitine palmitoyltransferase (CPT) as a rate-determining enzyme in β-oxidation of fatty acids was measured in brown adipose tissues. As shown in Table 4, the activity for the CLA-supplemented group was higher than that for the control group.

The above results show that feeding of CLA to rats can increase brown adipose tissues and can enhance carnitine palmitoyltransferase (CPT) activity without affecting the food intake and weight gain of rats. Therefore, CLA can be expected to consume extra energy and to generate heat, thereby exhibiting antiobesitic effect which is free from side effect and harmless to the human body.

TABLE 1

Composition of feed (AIN-93G)

| Ingredients | Experimental groups | |
|---|---|---|
| | Control group | CLA |
| | (g/100 g) | |
| Casein | 20.0 | 20.0 |
| Soybean oil | 6.0 | 6.0 |
| α-Cornstarch | 13.2 | 13.2 |
| Sucrose | 10.0 | 10.0 |
| Mineral mix (AIN-93G) | 3.5 | 3.5 |
| Vitamin mix (AIN-93VX) | 1.0 | 1.0 |
| L-Cystine | 0.3 | 0.3 |
| Choline tartrate | 0.25 | 0.25 |
| Cellulose | 5.0 | 5.0 |
| t-Butylhydroquinone | 0.0014 | 0.0014 |
| Cornstarch | 39.7 | 39.7 |
| LA (safflower oil) | 1.0 | — |
| CLA | — | 1.0 |

TABLE 2

CLA and fatty acid composition of safflower oil

| | CLA | Safflower oil |
|---|---|---|
| C16: 0 (palmitic acid) | 6.9 | 6.7 |
| C18: 0 (stearic acid) | 2.4 | 2.4 |
| C18: 1 (oleic acid) | 15.3 | 15.1 |
| C18: 2 (linoleic acid) | 0.7 | 74.1 |
| CLA (conjugated linoleic acid) | 74.1 | n.d. |
| c9, t11/t9, c11–18:2 | (34.1) | — |
| t10, c12–18:2 | (35.9) | — |
| c9, c11/c10, c12–18:2 | (2.5) | — |
| t9, t11/c10, t12–18:2 | (1.6) | — |
| C18: 3 (α-linolenic acid) | — | 0.5 |
| Others | 0.6 | 1.2 |

TABLE 3

Growth and weight of organs of rats

| Parameter | Experimental groups | |
|---|---|---|
| | Control group | CLA |
| Weight gain, g/4 weeks | 217 | 227 |
| Food intake, g/day | 21.0 | 21.0 |
| Weight of organs, g/100 g body weight | | |
| Liver | 4.36 | 4.40 |
| Kidney | 0.75 | 0.78 |
| Heart | 0.39 | 0.36 |
| Lung | 0.42 | 0.40 |
| Spleen | 0.22 | 0.22 |
| Brain | 0.40 | 0.38 |
| Peri-renal adipose tissue | 1.72 | 1.16 |
| Epididymal adipose tissue | 1.13 | 1.17 |
| Brown adipose tissue | 0.15 | 0.21 |

TABLE 4

Activity of carnitine-palmitin transferase (CPT) in brown adipose tissue

| Parameter | Experimental groups | |
|---|---|---|
| | Control group | CLA |
| CPT activity, μmol/min/total BAT (brown adipose tissue) | 192.5 | 239.1 |

What is claimed is:

1. A method for increasing the amount of brown fat in an animal in need thereof, comprising administering to said animal a conjugated linoleric acid (CLA) in an effective amount to increase said amount of brown fat.

2. The method according to claim 1, wherein said conjugated linoleic acid is selected from the group consisting of 9,11-octadecadienoic acid, 10,12-octadecadienoic acid, and a mixture thereof.

3. The method according to claim 1, wherein said conjugated linoleic acid is in the form of a fatty acid, a sodium salt, a potassium salt, a calcium salt, a triglyceride, a diglyceride, a monoglyceride, a phospholipid, or a mixture of two or more of said forms.

4. The method of claim 1, wherein said CLA in an effective amount to increase said amount of brown fat is in the form of a food or animal feed composition.

5. The method according to claim 4, wherein said food or feed composition is in the form of a conjugated linoleic acid-containing fat-and-oil product.

6. The method according to claim 5, wherein said fat-and-oil product is a safflower oil that has been subjected to an alkali conjugation reaction.

7. The method according to claim 4, wherein said food or feed composition is a pet food.

8. The method according to claim 1, wherein said CLA in an effective amount to increase said amount of brown fat is in the form of a pharmaceutical composition.

* * * * *